(12) United States Patent
Burnes

(10) Patent No.: US 7,107,093 B2
(45) Date of Patent: Sep. 12, 2006

(54) USE OF ACTIVATION AND RECOVERY TIMES AND DISPERSIONS TO MONITOR HEART FAILURE STATUS AND ARRHYTHMIA RISK

(75) Inventor: John E. Burnes, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 136 days.

(21) Appl. No.: 10/426,644

(22) Filed: Apr. 29, 2003

(65) Prior Publication Data

US 2004/0220635 A1    Nov. 4, 2004

(51) Int. Cl.
*A61B 5/04* (2006.01)
(52) U.S. Cl. .......................................... 600/509; 607/25
(58) Field of Classification Search .................. 607/25; 600/509
See application file for complete search history.

(56) References Cited

U.S. PATENT DOCUMENTS

| | | | |
|---|---|---|---|
| 4,550,502 A * | 11/1985 | Grayzel | 33/1 B |
| 4,569,357 A | 2/1986 | Sanz et al. | |
| 5,117,824 A | 6/1992 | Keimel et al. | |
| 5,257,621 A | 11/1993 | Bardy et al. | |
| 5,313,953 A | 5/1994 | Yomtov et al. | |
| 5,560,368 A | 10/1996 | Berger | |
| 5,560,370 A | 10/1996 | Verrier et al. | |
| 5,792,065 A | 8/1998 | Xue et al. | |
| 5,987,352 A | 11/1999 | Klein et al. | |
| 6,070,101 A | 5/2000 | Struble et al. | |
| 6,152,882 A | 11/2000 | Prutchi | |
| 6,438,409 B1 | 8/2002 | Malik et al. | |
| 6,456,880 B1 | 9/2002 | Park et al. | |
| 6,466,819 B1 | 10/2002 | Weiss | |
| 6,473,645 B1 | 10/2002 | Levine | |
| 6,522,904 B1 | 2/2003 | Milka et al. | |

OTHER PUBLICATIONS

Anastasiou-Nana, et al., "*Relation of Dispersion of QRS and QT in Patients with Advanced Congestive Heart Failure to Cardiac and Sudden Death Mortality*", The American Journal of Cardiology, vol. 85, May 15, 2002, pp. 1212-1217.

Millar, C.K., et al., "Correlation between refractory periods and activation-recovery intervals from electrograms: effects of rate and adrenergic interventions", Circ. 1985; 72:1372-9.

Haws, C.W., et al., "Correlation between in vivo transmembrane action potential durations and activation-recovery intervals from electrograms. Effects of interventions that alter repolarization time." Circ. 1990; 81:281-8.

(Continued)

*Primary Examiner*—Mark Bockeman
(74) *Attorney, Agent, or Firm*—Paul H. McDowell; Girma Wolde-Michael

(57) ABSTRACT

A system and method for monitoring electrical dispersion of the heart is provided including an implantable medical device and associated electrode system for sensing cardiac signals from a combination of two or more local and/or global EGM sensing vectors and/or subcutaneous ECG sensing vectors. Activation and recovery times and the activation-recovery intervals are measured from a selected cardiac cycle for each sensing vector. Dispersion is determined as the differences between activation times, recovery times and/or ARIs measured from each of the sensing vectors. An increase in dispersion indicates a worsening of heart failure and/or an increased risk of arrhythmias. Accordingly, a cardiac therapy may be delivered or adjusted in response to a detected increase in dispersion.

23 Claims, 12 Drawing Sheets

OTHER PUBLICATIONS

Gepstein, L., et al., "Activation-Repolarization Coupling in the Normal Swine Endocardium," Cir. 1997; 96:4036-4043.

Chinushi, M., et al., "Cycle Leng-Associated Modulation of the Regional Dispersion of Ventricular Repolarization in a Canine Model of Long QT Syndrome," *Journal of Pacing and Clinical Electrophysiology*, vol. 24, No. 8, Aug. 2001, pp. 1247-1257.

Burnes, J.E., et al., "Imaging Dispersion of Myocardial Repolarization, I Comparison of Body-Surface and Epicardial Measures," Circ. 2001; 104:1299-305.

Ghanem, R.N., et al., "Imaging Dispersion of Myocardial Repolarization, II Noninvasive Reconstruction of Eipcardial Measures," Circ. 2001; 104:1306-12.

Taggart, P., et al., "Transmural repolarisation in the left ventricle in humans during normoxia and ischaemia," from *Cardiovascular Research*, Circ. 201; 50:454-462.

Wantanabe, T., et al., "Regional prolongation of ARI and altered restitution properties cause ventricular arrhythmia in heart failure," from *Am J Physiol Heart Circ. Physiol.*, Circ. 2002; 282:H212-218.

Chinushi, M., et al., "Activation-Recovery Interval as a Parameter to Assess the Intracardiac Ventricular Repolarization in Patients with Congenital Long QT Syndrome," from *The American Journal of Cardiology*, vol. 90, Circ. 2002; 90:432-435.

Laurita, K.R., et al., "Modulation of Ventricular Repolarization by a Premature Stimulus," Circ. Res. 1996; 79:493-503.

Yu, C., et al., "Tissue Doppler Echocardiographic Evidence of Reverse Remodeling and Improved Synchronicity by Simultaneously Delaying Regional Contraction After Biventricular Pacing Therapy in Heart Failure," Circ. 2002; 105:438-435.

* cited by examiner

USE OF ACTIVATION AND RECOVERY TIMES AND DISPERSIONS TO MONITOR HEART FAILURE STATUS AND ARRHYTHMIA RISK

CROSS REFERENCE TO RELATED APPLICATIONS

This patent disclosure hereby incorporates by reference the following patent applications filed on even date hereof; namely, P-11214, "Method and Apparatus for Detecting Myocardial Electrical Recovery and Controlling Extra-Systolic Stimulation"; P-11216, "Method and Apparatus to Monitor Pulmonary Edema"; P-11252, Method and Apparatus for Determining Myocardial Electrical Resitution and Controlling Extra Systolic Stimulation; and P-11030, "Cardiac Pacing Therapy Parameter Programming".

FIELD OF THE INVENTION

The present invention relates generally to the field of monitoring electrical cardiac signals and more specifically to an implantable system and method for measuring myocardial electrical activation time and recovery time and dispersions thereof for use in monitoring heart failure status, monitoring arrhythmia risk or managing the delivery of a cardiac therapy.

BACKGROUND OF THE INVENTION

Increased variability, or "dispersion," of myocardial electrical activation and recovery times over the geography of the heart during a cardiac cycle is known to increase the propensity for cardiac arrhythmias. Times of activation, observed as the QRS signal on an ECG, and recovery, observed as the T-wave, can be measured on a multiple-lead surface ECG. Prolonged Q-T interval and interlead variability of the Q-T interval are strong predictors of cardiac arrhythmias. Repolarization dispersion as well as the orientation of repolarization gradients may be important determinants of the vulnerability to re-entrant tachycardias as previously reported several years ago in prior publications. Heart failure patients having greater dispersion of the QRS and the Q-T interval are reportedly at a greater risk for sudden cardiac death and have a lower chance of survival.

Non-invasive surface ECG studies can be performed for measuring QT interval dispersion. The difference and variance of the difference between a minimum and maximum Q-T interval measured using standard 12-lead ECG provide an index of dispersion. A long Q-T interval is a reflection of myocyte action potential prolongation. Action potential prolongation associated with heart failure, congenital long Q-T syndrome, and drug-induced effects is reportedly linked to increased dispersion of the activation-recovery interval (ARI) over the heart. The ARI can be defined as the interval between a point selected on the QRS wave to represent the activation time and a point selected on the T-wave to represent the recovery time on an ECG or cardiac electrogram (EGM) signal. Prolonged ARI and increased dispersion of activation, recovery and/or ARI create an important substrate for arrhythmias.

Thus, measurement of the dispersion of activation and recovery times and the ARI is of interest for a number of diagnostic and prognostic applications. A method and apparatus for non-invasive dynamic tracking and diagnosing of cardiac vulnerability to ventricular fibrillation using leads placed on the surface of the chest for simultaneous assessment of T-wave alternans, Q-T interval dispersion, and heart rate variability are generally disclosed in U.S. Pat. No. 5,560,370 issued to Verrier et al. A method and apparatus for analyzing QT dispersion in ECG lead signals is generally disclosed in U.S. Pat. No. 5,792,065, issued to Xue et al., in which T-wave markers are determined automatically for making Q-T dispersion measurements from ECG signals. However, it is desirable to provide chronic ambulatory, monitoring of electrical dispersion in heart failure patients or in patients having other conditions known to cause a propensity for arrhythmias such that a worsening of the patient's disease status or arrhythmia risk may be quickly diagnosed and treated.

Methods for chronically measuring action potential duration are generally disclosed in U.S. Pat. No. 6,152,882 issued to Prutchi and in U.S. Pat. No. 6,522,904 issued to Mika. A cardioelectric apparatus for the early detection of a tachycardia is generally disclosed in U.S. Pat. No. 6,466,819 issued to Weiss wherein time-variant measurements of paired heart rate and action potential duration measurements are compared for determining a tachycardia risk. Geographic dispersion of action potential duration at a point in time is not disclosed. An implantable cardiac stimulation device that monitors progression or regression of a patient's heart condition by determining ventricular repolarization interval dispersions spaced apart over time is generally disclosed in U.S. Pat. No. 6,456,880 issued to Park et al. The ventricular repolarization interval dispersions are determined based upon the difference between a maximum ventricular repolarization interval measured with one of a plurality of electrode configurations and a minimum ventricular repolarization interval measured with another one of the plurality of electrode configurations. The plurality of electrode configurations selected include electrodes positioned in both the right and left side of the heart to preclude localized sensing.

However, localized measurement of activation and recovery times at two or more sites for determining electrical dispersion provide more accurate and site-specific information compared to measurements made from relatively global signals. Determination of the ARI from a unipolar EGM signal is closely correlated to the duration of the local monophasic action potential. Furthermore, differences between localized measurements of activation and recovery times made at two or more sites during the same cardiac cycle provide an accurate measurement of the geographic dispersion of activation and recovery and the orientation of the dispersion.

Chronic, ambulatory monitoring of the heterogeneity of activation and refractoriness could also be useful in managing the delivery of a number of cardiac therapies. Cardiac resynchronization therapy (CRT) has been clinically demonstrated to improve indices of cardiac function in patients suffering from congestive heart failure. Cardiac pacing may be applied to one or both ventricles or multiple heart chambers, including one or both atria, to improve cardiac chamber coordination, which in turn improves stroke volume and pumping efficiency. Clinical follow-up of patients undergoing resynchronization therapy has shown improvements in hemodynamic measures of cardiac function, left ventricular volumes, and wall motion. However, not all patients respond favorably to cardiac resynchronization therapy. Physicians are challenged in selecting patients that will benefit and in selecting the optimal pacing intervals applied between the atria and ventricles (A-V intervals) and between the left and right ventricles (V-V intervals) to resynchronize the heart chamber contractions.

Selection of pacing intervals may be based on echocardiographic studies performed acutely to determine the settings resulting in the best hemodynamic response. It can be reasonably assumed that improved mechanical coordination gained from CRT therapy is associated with reduced dispersion of electrical activity as well. Therefore a method for optimizing CRT pacing intervals based on reducing electrical dispersion of activation, recovery, or the interval between activation and recovery (ARI) is desirable.

From the above discussion, it is apparent that a need remains for a method and associated apparatus for monitoring dispersion of electrical activation and recovery based on local or global cardiac signals or both. Assessment of electrical dispersion is useful in monitoring heart failure status and arrhythmia risk. Analysis of activation and recovery time and ARI dispersion would also be useful in controlling the delivery of anti-arrhythmic drugs or other pharmaceutical agents or other types of therapies, such as spinal cord stimulation, that affect the electrical activity of the heart or have autonomic influences on the heart. It is further desirable to provide a method for controlling the timing of cardiac resynchronization therapy so as to increase the homogeneity of electrical activation and recovery.

SUMMARY OF THE INVENTION

The present invention provides a system and method for measuring activation and recovery times, ARI and the dispersion of the these parameters in an implantable device for use in assessing a patient's disease state and/or adjusting a therapy in order to reduce dispersion and in turn reduce the risk of arrhythmias or optimize delivery of the therapy. The system includes an implantable device capable of sensing a number of EGM or subcutaneous ECG signals received from selected sensing electrodes located on one or more associated cardiac leads or on the device itself. The implantable device is further capable of determining an activation time, a recovery time, and an ARI from each of the EGM signals for a given cardiac cycle. Sensing electrodes are selected for sensing local unipolar EGM signals and/or local bipolar EGM signals. In addition, relatively more global integrated bipolar EGM signals, or relatively more global ECG signals detected using subcutaneous ECG electrodes may be selected.

Activation time is measured as the time that a selected feature of the QRS signal occurs, which may be a peak, maximum positive slope, maximum negative slope, crossing of a predetermined threshold or other fiducial point. Recovery time is measured as the time that a selected feature of the T-wave occurs, which may be a maximum positive derivative, maximum negative derivative, peak, trough, end point, crossing of a predetermined threshold or other fiducial point. The ARI is the difference between the activation time and the recovery time measured from a sensed EGM or ECG signal during a given cardiac cycle.

Dispersions of activation, recovery and ARI are determined as the differences between activation times, recovery times and ARIs, respectively, measured from each sensed EGM and ECG signal during a given cardiac cycle. Dispersion of activation and recovery times may be determined relative to the earliest activation time detected, designated as "time 0" with all later sensed activation times and recovery times determined relative to the earliest activation time. In the case of a paced cardiac cycle, the "time 0" could be defined as the time of the pace. Dispersion of activation, recovery, and ARI are determined for a given cardiac cycle during a monitoring episode. Activation and recovery time measurements may be made for a number of cardiac cycles during a monitoring episode and may be analyzed for determining averages or deviations of the dispersions for a particular monitoring episode. Dispersion measurements are stored for comparison to dispersion measurements made during previous monitoring episodes. The heart rate, patient activity levels, and/or other physiologic information may be recorded as well so as to make relative comparisons of the dispersion measurements more meaningful.

Increases in dispersion of activation, recovery, and/or ARI indicate an overall worsening of a cardiovascular condition or arrhythmia risk. Detection of increased dispersion may generate a patient and/or physician warning, trigger the delivery of a therapy, or cause adjustment of a therapy.

DETAILED DESCRIPTION OF THE INVENTION

The present invention is directed toward providing an implantable system for monitoring dispersion of activation, recovery and the activation recovery interval (ARI). The implantable system includes a set of electrodes, which may be located on one or more cardiac leads, for measuring EGM or ECG signals and an implantable medical device for receiving the signals and processing the signals to determine the dispersion of activation, recovery and/or ARI. The implantable device may be embodied as a monitoring device for receiving EGM and/or ECG signals and storing activation and recovery time data and measured dispersions. The implantable device may alternatively be a monitor and therapy delivery device. In one embodiment, the device is a monitor and stimulator capable of monitoring electrical dispersion and delivering a stimulation therapy such as cardiac pacing, cardiac resynchronization therapy (CRT), anti-tachycardia pacing, and/or cardioversion and defibrillation therapies. The implantable device may alternatively provide other types of therapies such as spinal cord stimulation or drug delivery for treating heart failure or arrhythmias.

Figure 1A:
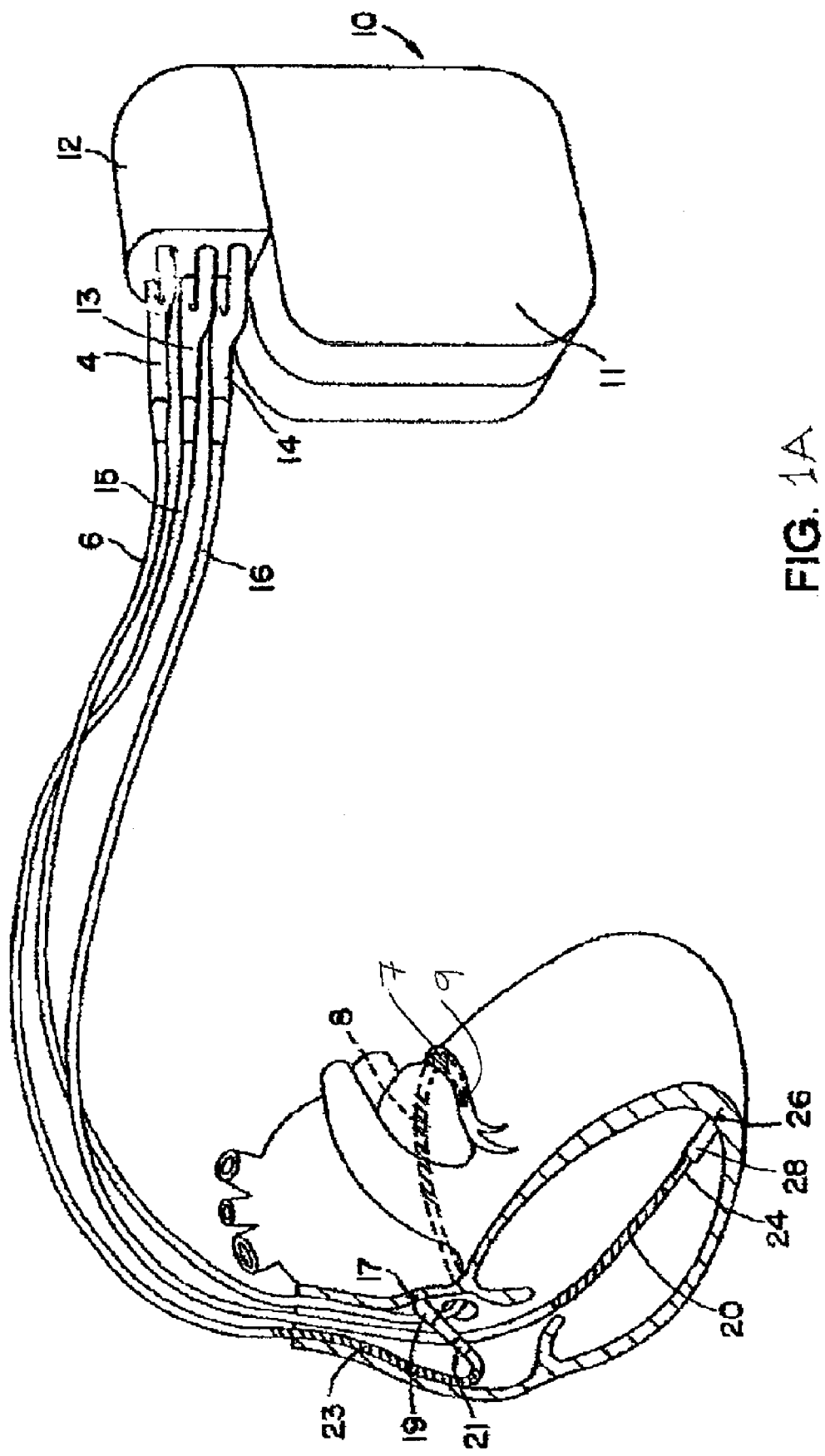
FIG. 1A is an illustration of an exemplary implantable medical device (IMD) coupled to a patient's heart by three cardiac leads.

FIG. 1A is an illustration of an exemplary implantable medical device (IMD) coupled to a patient's heart by three cardiac leads. IMD 10 is capable of receiving cardiac signals for monitoring purposes and delivering electrical pulses for cardiac pacing, cardioversion and defibrillation. IMD 10 includes a connector block 12 for receiving the proximal end of a right ventricular lead 16, a right atrial lead 15 and a coronary sinus lead 6, used for positioning electrodes for sensing and stimulation in three or four heart chambers. In FIG. 1A, the right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to IMD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. Coronary sinus lead 6 is also equipped with a distal tip electrode 9 and ring electrode 7 for pacing and sensing functions in the left chambers of the heart. The coil electrode 8, tip electrode 9 and ring electrode 7 are each coupled to insulated conductors within the body of lead 6, which provides connection to the proximal bifurcated connector 4.

The electrodes 17 and 21, 24 and 26, and 7 and 9 may be used in sensing and stimulation as bipolar pairs, commonly referred to as a "tip-to-ring" configuration, or individually in a unipolar configuration with the device housing 11 serving as the indifferent electrode, commonly referred to as the "can" or "case" electrode. If IMD 10 is intended for delivering high-voltage cardioversion and defibrillation therapies, device housing 11 may also serve as a subcutaneous defibrillation electrode in combination with one or more of the defibrillation coil electrodes 8, 20,23 for defibrillation of the atria or ventricles.

For the purposes of measuring of activation and recovery times in accordance with the present invention, bipolar "tip-to-ring" sensing vectors, unipolar tip-to-can sensing vectors, and vectors between any available tip or ring electrode to a coil electrode are used to sense a local EGM signal at the site of the sensing electrode. A "biventricular unipolar" sensing vector could be established between a tip or ring electrode located on right ventricular lead 16 and a tip or ring electrode located on coronary sinus lead 6 for sensing a local EGM signal. Coil electrodes 8,20,23 may be paired with the device housing 11 for sensing relatively more global EGM vectors for measuring more global activation and recovery times.

It is recognized that alternate lead systems may be substituted for the three lead system illustrated in FIG. 1A. For example, lead systems for sensing multiple EGM vectors within a heart chamber may include multiple unipolar or bipolar leads and/or one or more multipolar leads positioned in operative relation to one heart chamber. Lead systems for sensing EGM vectors within multiple heart chambers may include one or more unipolar, bipolar or multipolar leads positioned relative to the multiple heart chambers. Both local and global EGM signals may be used for monitoring the heterogeneity of activation and recovery of the myocardium in one or both ventricles.

Figure 1B:
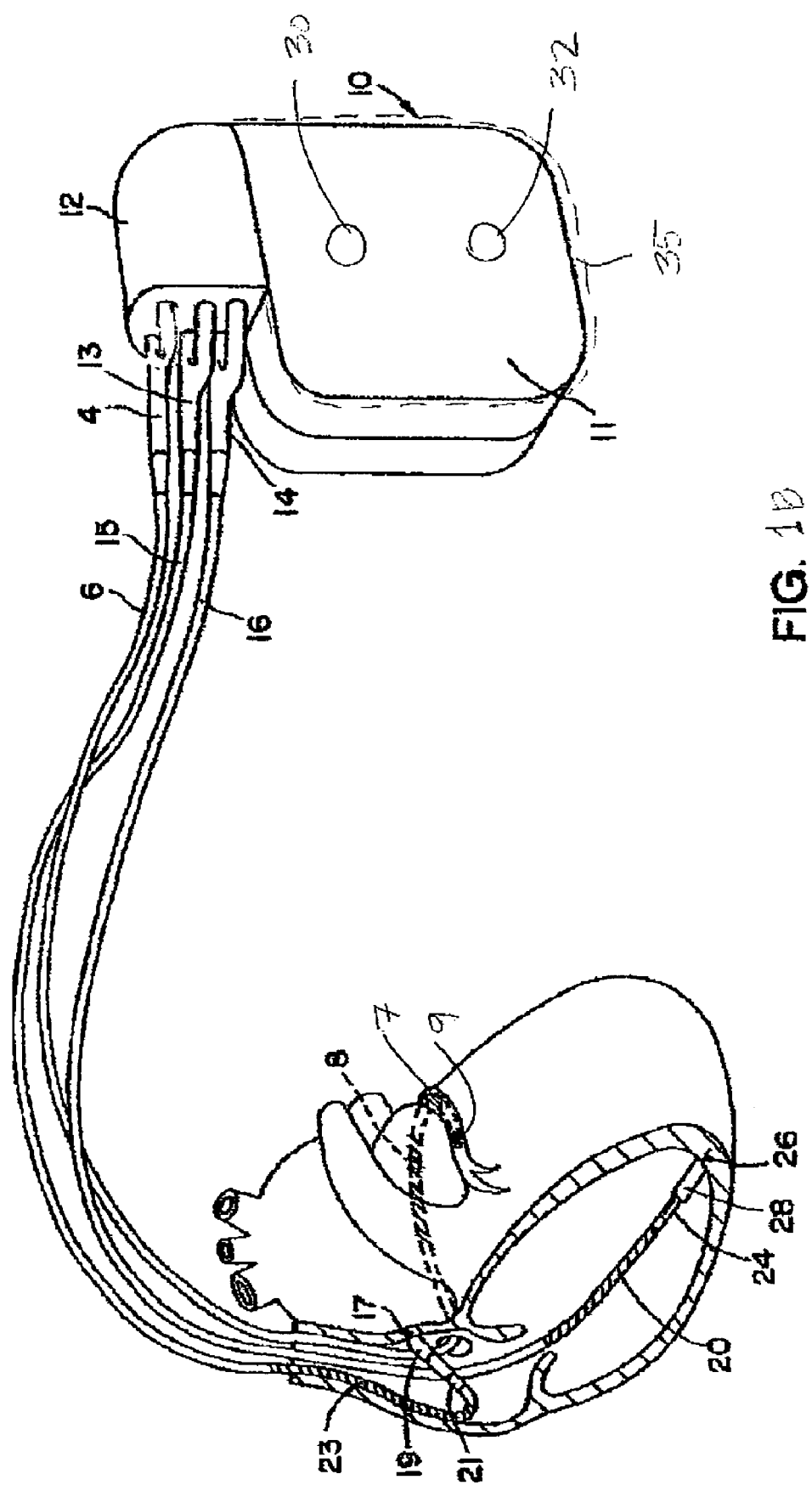
FIG. 1B is an illustration of an alternative IMD that includes subcutaneous ECG electrodes and is coupled to a set of leads implanted in a patient's heart.

FIG. 1B is an illustration of an alternative IMD coupled to a set of leads implanted in a patient's heart. In FIG. 1B, IMD housing 11 is provided with an insulative coating 35 with openings 30 and 32. The uninsulated openings 30 and 32 serve as subcutaneous electrodes for sensing global ECG signals, which may be used, in accordance with the present invention, in measuring global activation and recovery times for analyzing electrical dispersion. An implantable system having electrodes for subcutanteous measurement of an ECG is generally disclosed in commonly assigned U.S. Pat. No. 5,987,352 issued to Klein, incorporated herein by reference in its entirety. In alternative embodiments, multiple subcutaneous electrodes incorporated on the device housing 11 or positioned on subcutaneous leads extending from IMD 10 may be used to acquire multiple subcutaneous ECG sensing vectors for measurement of electrical dispersion. Multi-electrode ECG sensing in an implantable monitor is described in U.S. Pat. No. 5,313,953 issued to Yomtov, et al., incorporated herein by reference in its entirety.

While a particular multi-chamber IMD and lead system is illustrated in FIGS. 1A and 1B, methodologies included in the present invention may adapted for use with other single chamber, dual chamber, or multichamber IMDs or pacemaker systems, or other cardiac monitoring devices.

Figure 2:
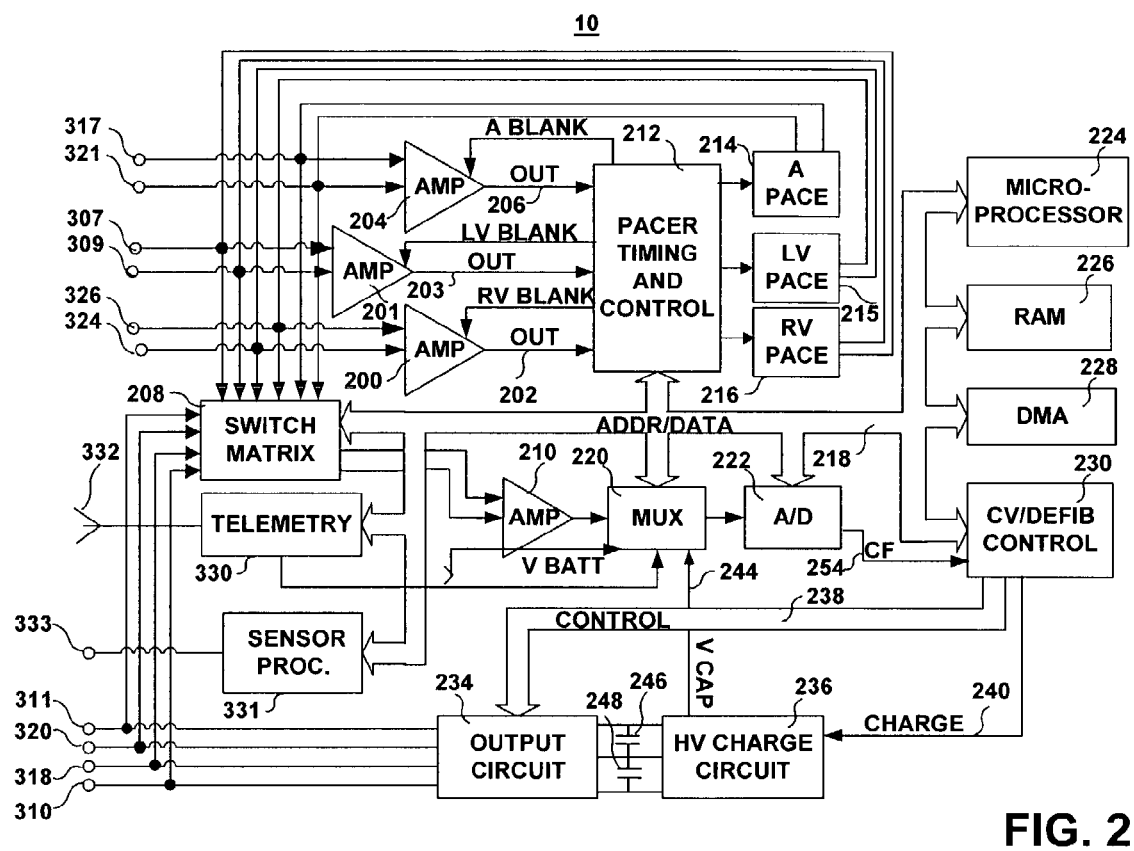
FIG. 2 is a functional schematic diagram of the IMD of FIG. 1A.

A functional schematic diagram of the IMD 10 is shown in FIG. 2. This diagram should be taken as exemplary of the type of device in which the invention may be embodied and not as limiting. The disclosed embodiment shown in FIG. 2 is a microprocessor-controlled device, but the methods of the present invention may also be practiced in other types of devices such as those employing dedicated digital circuitry.

With regard to the electrode system illustrated in FIG. 1A, the IMD 10 is provided with a number of connection terminals for achieving electrical connection to the leads 6,15,16 and their respective electrodes. The connection terminal 311 provides electrical connection to the housing 11 for use as the indifferent electrode during unipolar stimulation or sensing. The connection terminals 320,310,318 provide electrical connection to coil electrodes 20,8,23 respectively. Each of these connection terminals 311, 320,310,318 are coupled to the high voltage output circuit 234 to facilitate the delivery of high energy shocking pulses to the heart using one or more of the coil electrodes 8,20,23 and optionally the housing 11.

The connection terminals 317,321 provide electrical connection to the helix electrode 17 and the ring electrode 21 positioned in the right atrium. The connection terminals 317,321 are further coupled to an atrial sense amplifier 204 for sensing atrial signals such as P-waves. The connection terminals 326,324 provide electrical connection to the helix electrode 26 and the ring electrode 24 positioned in the right ventricle. The connection terminals 307,309 provide electrical connection to tip electrode 9 and ring electrode 7 positioned in the coronary sinus. The connection terminals 326,324 are further coupled to a right ventricular (RV) sense amplifier 200, and connection terminals 307,309 are further coupled to a left ventricular (LV) sense amplifier 201 for sensing right and left ventricular signals, respectively.

The atrial sense amplifier 204 and the RV and LV sense amplifiers 200 and 201 preferably take the form of automatic gain controlled amplifiers with adjustable sensing thresholds. The general operation of RV and LV sense amplifiers 200 and 201 and atrial sense amplifier 204 may correspond to that disclosed in U.S. Pat. No. 5,117,824, by Keimel, et al., incorporated herein by reference in its entirety. Generally, whenever a signal received by atrial sense amplifier 204 exceeds an atrial sensing threshold, a signal is generated on output signal line 206. Whenever a signal received by RV sense amplifier 200 or LV sense amplifier 201 that exceeds an RV or LV sensing threshold, respectively, a signal is generated on the corresponding output signal line 202 or 203.

In one embodiment of the present invention, ventricular sense amplifiers 200,201 may include separate, dedicated sense amplifiers for sensing R-waves and T-waves, each using adjustable sensing thresholds. Activation times used for measuring electrical dispersion may be measured when a signal exceeding an R-wave sensing threshold is received by an R-wave sense amplifier included in RV or LV sense amplifiers 200 or 201, causing a corresponding R-sense signal to be generated on signal line 202 or 203, respectively. Likewise, recovery times used for measuring electrical dispersion may be measured when a signal exceeding a T-wave sensing threshold is received by a T-wave sense amplifier included in RV or LV sense amplifiers 200 or 201, causing a corresponding T-sense signal to be generated on signal line 202 or 203, respectively.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the IMD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228.

Microprocessor 224 may employ digital signal analysis techniques to characterize the digitized signals stored in random access memory 226 to recognize and classify the patient's heart rhythm employing any of the numerous signal processing methodologies known in the art. In accordance with the present invention, digital signal analysis of selected EGM (or subcutaneous ECG signals if available) is performed by microprocessor 224 to measure activation and recovery times for determining electrical dispersion as will be described in greater detail below. In one embodiment of the present invention, any available electrodes may be selected in pairs by switch matrix 208 for use in determining activation and recovery times employing digital signal analysis methods applied to the selected EGM signal(s).

The telemetry circuit 330 receives downlink telemetry from and sends uplink telemetry to an external programmer, as is conventional in implantable medical devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of RV R-waves, LV R-waves or atrial P-waves as indicated by signals on lines 202, 203 and 206, respectively. In accordance with the selected mode of pacing, pacing pulses are generated by atrial pacer output circuit 214, right ventricular pacer output circuit 216, and left ventricular pacer output circuit 215. During cardiac resynchronization therapy (CRT), pacer timing and control 212 controls the delivery of atrial-biventricular cardiac pacing pulses at selected atrial-ventricular (A-V) and ventricular-ventricular (V-V) intervals, also referred to collectively as "A-V-V intervals" intended to improve heart chamber synchrony. The escape intervals used in controlling the delivery of CRT pacing pulses by IMD 10 may be defined according to programmable timing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. In accordance with the present invention, selection and/or automatic adjustment of timing intervals is based on a determination of the dispersion of activation time, recovery time or ARI. A-V-V timing intervals producing the least dispersion can be selected as the operating parameters. The pacer output circuits 214, 215 and 216 are coupled to the desired electrodes for pacing via switch matrix 208. The escape interval counters are reset upon generation of pacing pulses, and thereby control the basic timing of cardiac pacing functions, including bradycardiac pacing, CRT, and anti-tachycardia pacing.

The durations of the escape intervals are determined by microprocessor 224 via data/address bus 218. The value of the count present in the escape interval counters when reset by sensed R-waves or P-waves can be used to measure R—R intervals and P—P intervals for detecting the occurrence of a variety of arrhythmias.

The microprocessor 224 includes associated ROM in which stored programs controlling the operation of the microprocessor 224 reside. A portion of the memory 226 may be configured as a number of recirculating buffers capable of holding a series of measured intervals for analysis by the microprocessor 224 for predicting or diagnosing an arrhythmia. Memory buffers may also be used to temporarily store activation times and recovery times measured from two or more sensing vectors for use in measuring ARIs and dispersion of activation, recovery and ARIs.

In response to the detection of tachycardia, anti-tachycardia pacing therapy can be delivered by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

Figure 3:
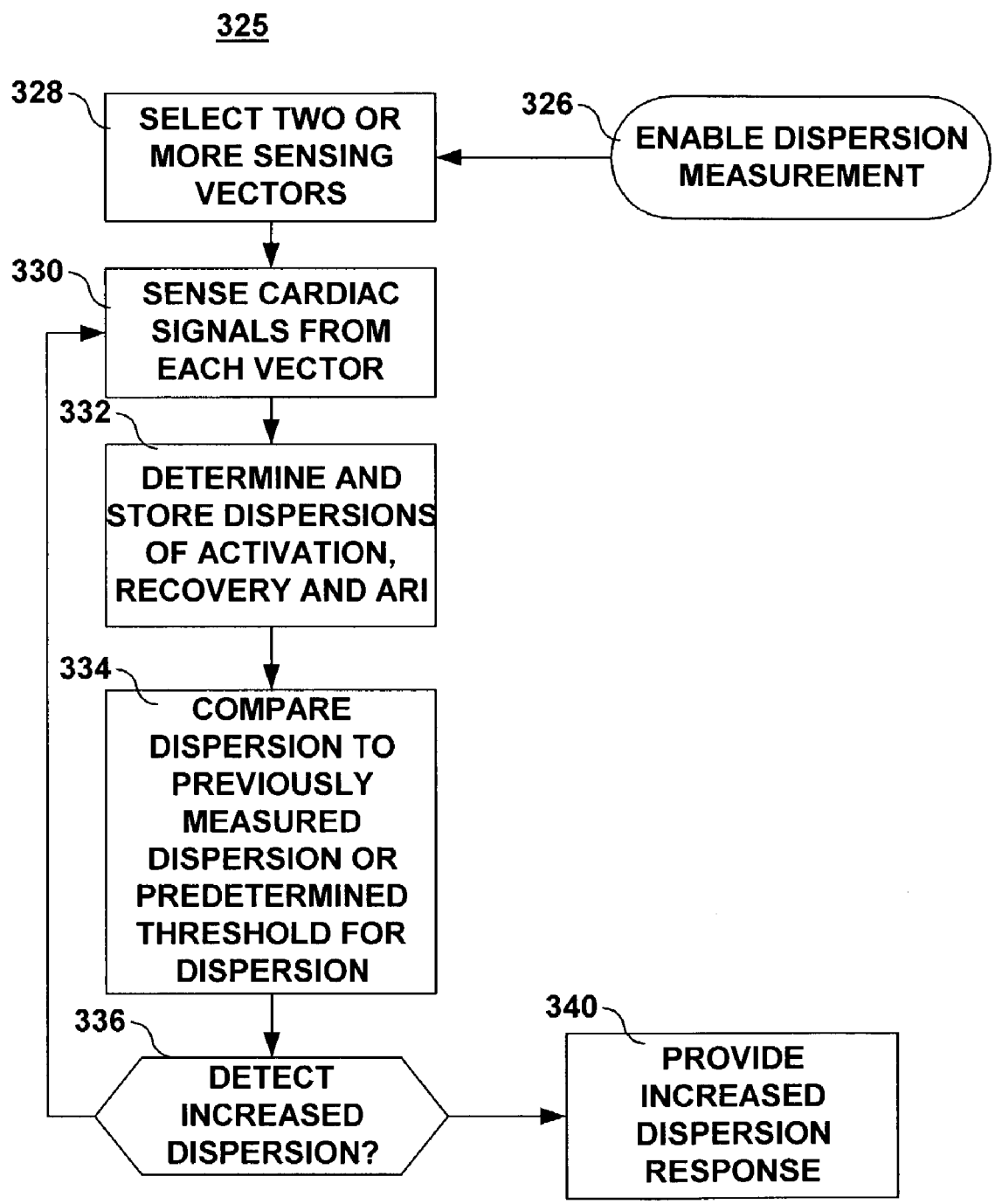
FIG. 3 is a flow diagram providing an overview of operations included in the present invention for determining and responding to dispersion of electrical activation, recovery and/or activation-recovery intervals (ARIs).

FIG. 3 is a flow diagram providing an overview of operations included in the present invention for determining dispersion of activation, recovery and/or ARIs. At step 326, method 325 waits for dispersion monitoring to be enabled. Dispersion measurements may be performed on a periodic basis for monitoring heart failure status, monitoring arrhythmia risk, or optimizing a therapy in order to reduce dispersion, for example by adjusting cardiac pacing parameters during CRT or adjusting the dosage of a drug therapy.

Once enabled, two or more sensing vectors are selected from the available electrodes of the associated lead system at step 328. Sensing vectors may include local sensing vectors, global sensing vectors, or both. Local sensing vectors include unipolar and bipolar EGM sensing configurations. Global sensing vectors include coil-to-can type EGM sensing configurations and subcutaneous ECG sensing configurations. Multiple vectors may be selected for measuring dispersion within a heart chamber, for example either the right or left ventricle. For measuring dispersion between both ventricles, one or more vectors are selected for sensing right ventricular EGM signals, and one or more vectors are selected for sensing left ventricular EGM signals. Additionally or alternatively, one ore more local sensing vectors can be selected along with one or more global sensing vectors to allow comparisons of a local activation time, recovery time and ARI to a globally measured activation time, recovery time and ARI. Likewise, two or more local sensing vectors can be selected along with two or more global sensing vectors to allow comparisons of local dispersions in activation time, recovery time and/or ARI to global dispersions in activation time, recovery time and/or ARI.

At step 330, the cardiac signals from each of the selected vectors are received by the associated IMD for signal processing. At step 332, the activation, recovery and ARI dispersions are determined and stored in device memory based on the ARIs measured from each selected vector for each detected cardiac cycle during the time of monitoring. Details regarding methods for determining these dispersions will be described below. Stored dispersion data, which may include time and date information, heart rate, physical activity, or other physiological or device operational parameters, is available for uplinking to an external device for review by a clinician.

At step 334, the measured dispersions are evaluated by the IMD to determine if a worsening of dispersion is evident. A measured dispersion can be compared to a previously measured dispersion at step 334. Alternatively, a measured dispersion may be compared to a predetermined acceptable dispersion threshold. At decision step 336, method 325 determines if dispersion has worsened as indicated by an increase in dispersion. If a measured dispersion is approximately equal to or less than a previously measured dispersion, or alternatively below a predetermined threshold value, dispersion has not worsened, and method 325 returns to step 310 to continue sensing cardiac signals from the selected sensing vectors for monitoring changes in dispersion If a measured dispersion is greater than the acceptable threshold, or has increased compared to a previously measured dispersion, wherein such increase may be required to be greater than some predetermined amount, then an increase or worsening in dispersion is detected at decision step 336. The IMD may optionally provide a response to the increased dispersion at step 340.

A response to increased dispersion, in one embodiment, is a warning flag generated to notify a clinician of the change in dispersion, which can indicate a worsening of heart failure status or increased arrhythmia risk. In another embodiment, the response additionally or alternatively triggers the delivery of a therapy. Triggered therapies may include, but are not limited to, a cardiac pacing therapy such as CRT, an arrhythmia prevention therapy such as overdrive pacing, spinal cord stimulation, or drug delivery. If a therapy is already being delivered upon detecting an increased dispersion, the increased dispersion response may include an adjustment to the therapy delivery. In yet another embodiment, the increased dispersion response may include adjusting arrhythmia detection parameters. Because the risk of arrhythmia is increased with increased dispersion, a heightened alert mode may be enabled such that arrhythmia detection algorithms quickly detect an arrhythmia. A "high alert" mode for arrhythmia detection that may be adapted for use with the present invention is generally described in U.S. patent application Ser. No. P-10215.00 to DeGroot and Burnes, incorporated herein by reference in its entirety.

Figure 4:
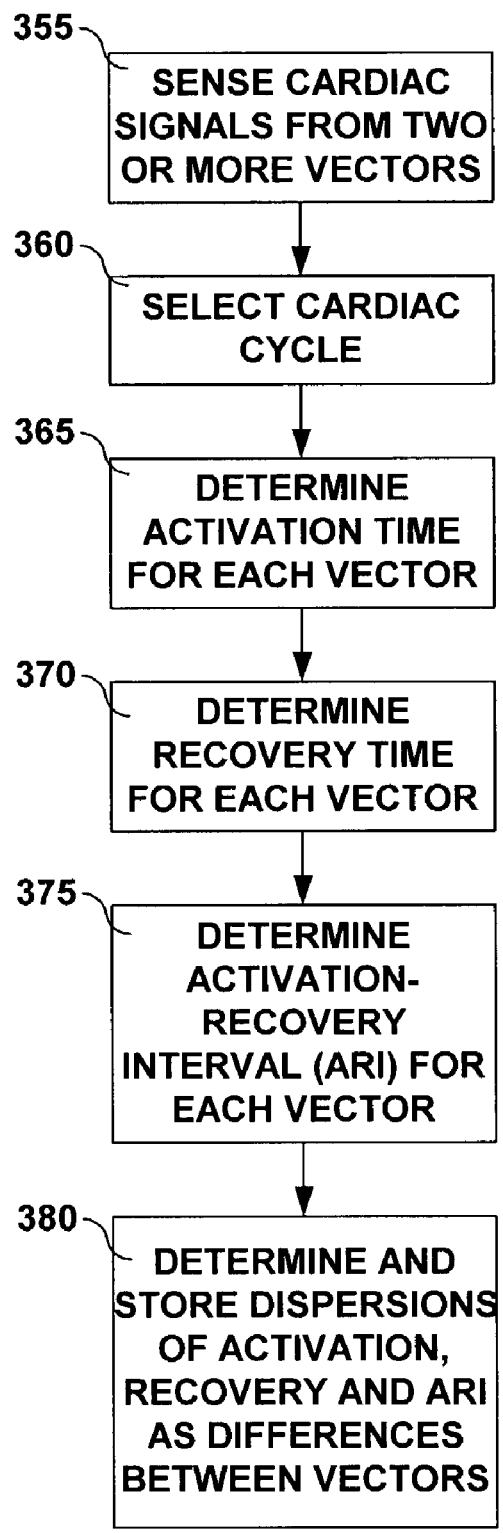
FIG. 4 is a flow chart summarizing the steps included in a method for measuring dispersion that may be used by the method of FIG. 3 according to one embodiment of the present invention.
Figure 5A:
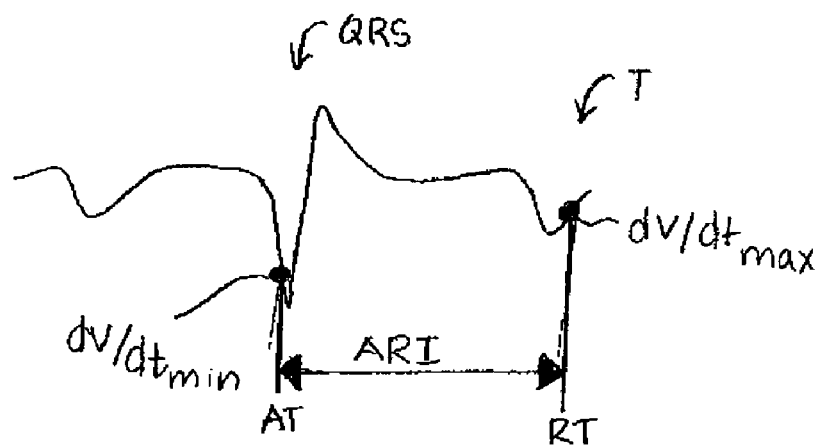
FIG. 5 depicts a representative unipolar EGM signal illustrating one method for measuring activation time, recovery time, and activation recovery interval.

FIG. 4 is a flow chart summarizing the steps included in a method for measuring dispersion that may be used by method 325 of FIG. 3 according to one embodiment of the present invention. At step 355, the cardiac signals from two or more selected sensing vectors are received by the associated IMD. At step 360, a single cardiac cycle to be analyzed is selected. At step 365, the activation times for each sensed vector during the selected cardiac cycle are determined. The activation time for a given EGM or subcutaneous ECG signal is determined as the time of a fiducial point on the QRS complex. The QRS signal may result from an intrinsic depolarization or an evoked response to a pacing pulse. A fiducial point for measuring activation time may be selected as a minimum or maximum peak, a minimum or maximum derivative, a threshold crossing, a zero crossing or other identifiable characteristic of a QRS signal. The fiducial point used to detect activation time of an intrinsic depolarization may be different than or the same as the fiducial point used to detect activation time of an evoked depolarization. A reference time 0 may be flagged as the earliest activation time detected from the selected sensing vectors. If activation time is measured following a pacing pulse, the time of pacing pulse delivery may be flagged as a reference time 0.

At step 370, the recovery times for each sensed vector during the selected cardiac cycle are determined. The recovery time is measured as the time of a fiducial point on the T-wave of the EGM or subcutaneous ECG signal. A maximum or minimum peak, a maximum or minimum derivative, the end point of the T-wave, or other identifiable characteristic point may be selected as the fiducial point for measuring recovery time. The recovery time may be measured relative to the flagged reference time 0.

The ARIs for each sensing vector are calculated at step 375 as the difference between the activation time and the recovery time determined for the respective vector. At step 380, dispersion of one or more of the measured parameters, namely activation time dispersion, recovery time dispersion, and/or ARI dispersion, are determined. Dispersion is measured as the difference(s) between measured parameter values for each sensing vector. If two sensing vectors are selected, dispersion is measured as the difference between the measured parameter values on the two vectors. In one embodiment, dispersions of activation, recovery and/or ARI between the right and left ventricles are measured by sensing a local unipolar EGM signal from the right ventricle and a second local unipolar EGM signal from the left ventricle. RV and LV activation and recovery times are measured during a selected cardiac cycle from the sensed RV and LV EGM signals. The difference between the RV and LV activation times, the RV and LV recovery times, and/or the RV and LV ARIs are calculated.

If multiple sensing vectors are selected for multichamber or multisite dispersion measurements, the differences between each pair of vectors may be determined and stored for evaluating the dispersion. Alternatively, the differences between the parameter value for each sensing vector and a reference vector may be stored. The reference vector may be the vector associated with the earliest activation, a global vector or other designated reference vector. The magnitude of dispersions in activation time, recovery time and/or ARI as well as the orientation of the gradients of dispersion may be of interest in evaluating the heart condition. Dispersion data are stored in memory of the implanted device for later review by a clinician. Data may include sensing vector notations, time and date, patient heart rate, and other physiological or device operational parameters.

Alternatively, the minimum and maximum values for a given parameter measured during the selected cardiac cycle from each vector are identified, and dispersion is measured as the difference between the minimum and maximum parameter values. The maximum and minimum measurements and/or the difference between the maximum and minimum and the associated vectors from which the maximum and minimum values were measured can be stored for later review by a clinician.

FIG. 5 depicts a representative unipolar EGM signal illustrating one method for measuring activation time, recovery time, and activation recovery interval. In this example, the fiducial point for measuring activation time (AT) is selected as the maximum negative derivative of the QRS signal, dV/dtmin. The fiducial point selected for measuring recovery time (RT) is selected as the maximum positive derivative of the T-wave, dV/dtmax. The difference between the AT and RT is determined as the ARI. ARI measured as the interval on a unipolar EGM between the maximum negative derivative of the QRS signal and the maximum positive derivative of the T-wave has been shown to be closely correlated to the duration of the local monophasic action potential. See Millar et al., Circulation, 1985. Thus, this measurement of local activation times and recovery times from a unipolar EGM is useful for chronic, ambulatory monitoring of dispersion in an implantable medical device.

Figure 6:
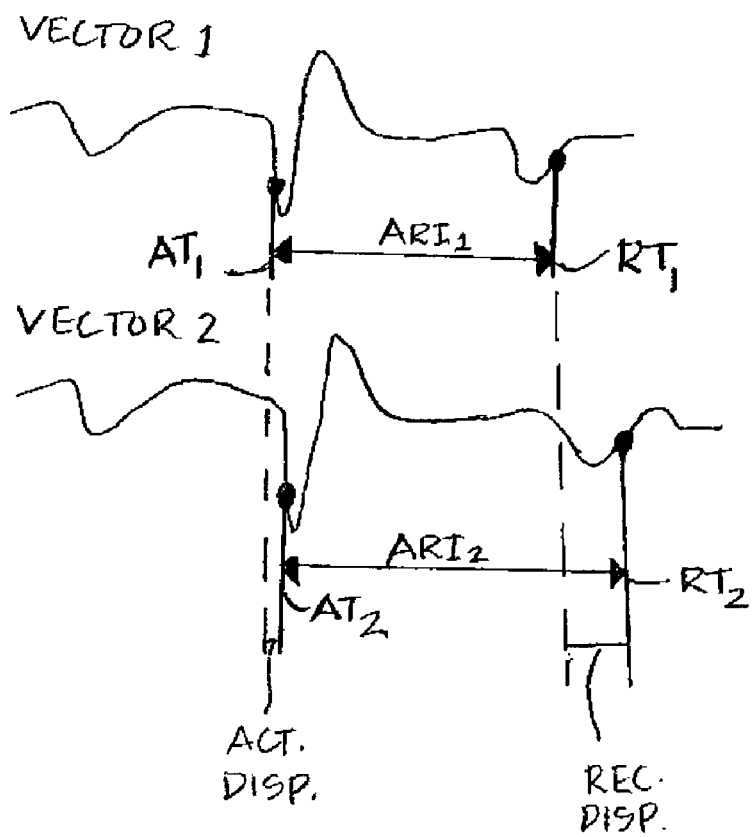
FIG. 6 illustrates two representative unipolar EGM signals measured from two different sensing vectors during a selected cardiac cycle.
Figure 5B:
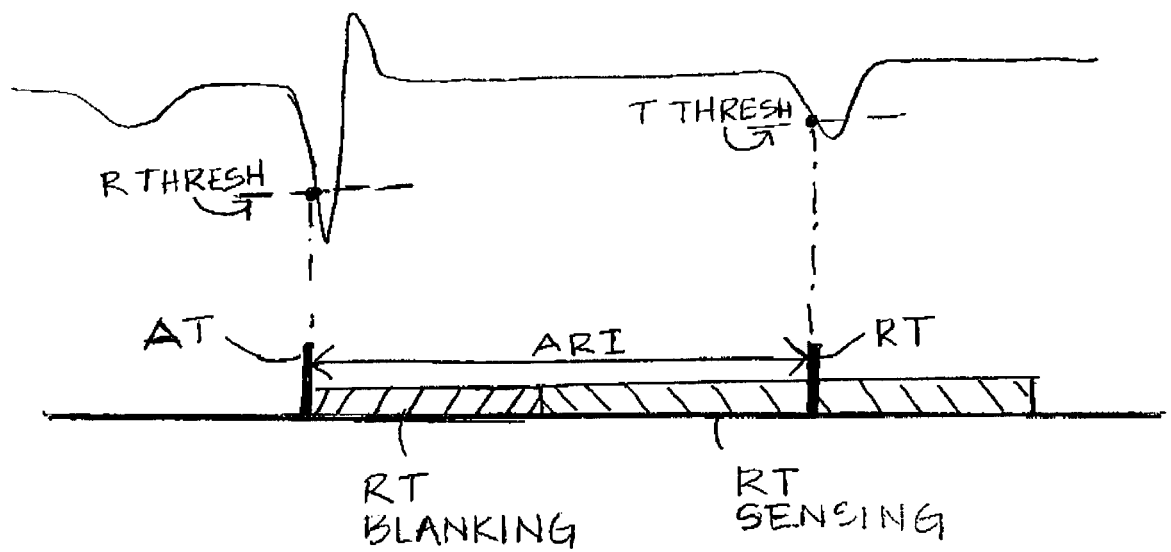
Figure 5C:
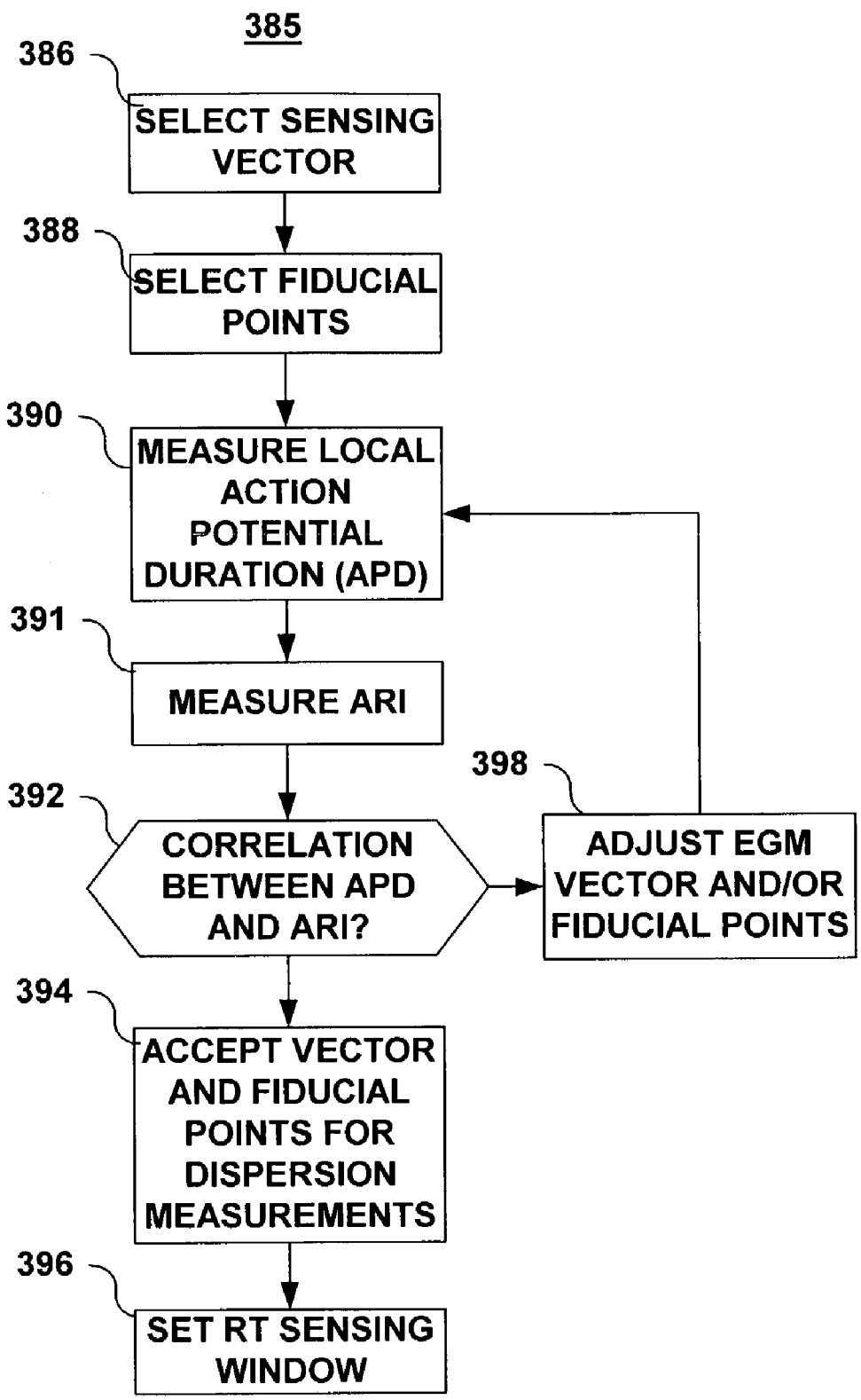
Figure 5D:
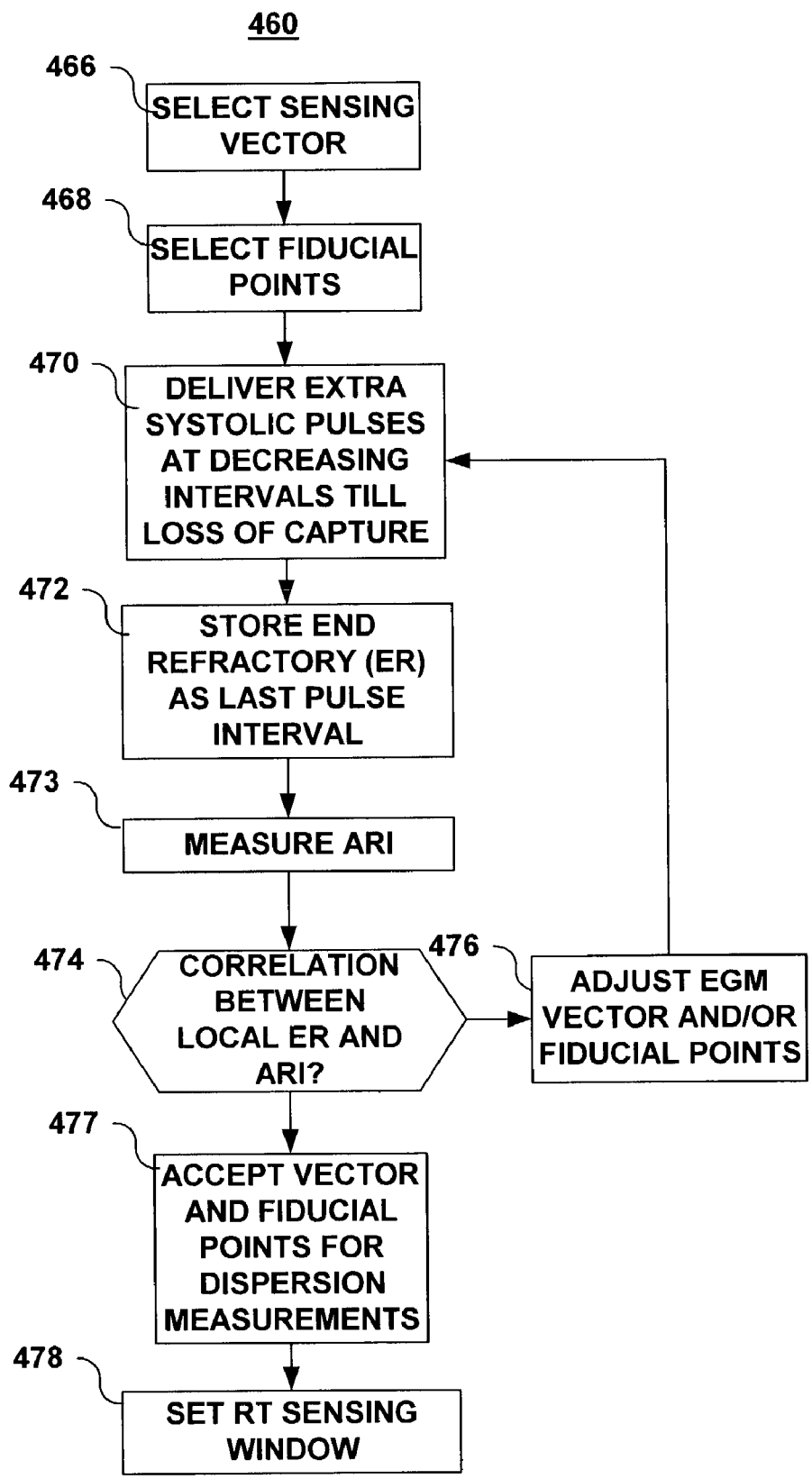

FIG. 6 illustrates two representative unipolar EGM signals measured from two different sensing vectors during a selected cardiac cycle. A first activation time, $AT_1$; a first recovery time, $RT_1$; and a first activation-recovery interval, $ARI_1$, are measured from a first sensing vector (VECTOR 1) during the selected cardiac cycle. A second activation time, $AT_2$; a second recovery time, $RT_2$; and second activation-recovery interval, $ARI_2$, are measured from a second sensing vector (VECTOR 2) during the same selected cardiac cycle. The activation dispersion (ACT. DISP) is the difference between the first and second activation times. The recovery dispersion (REC. DISP) is the difference between the first and second recovery times, and the ARI dispersion (not indicated in FIG. 6) is the difference between the first and second ARIs.

Figure 7:
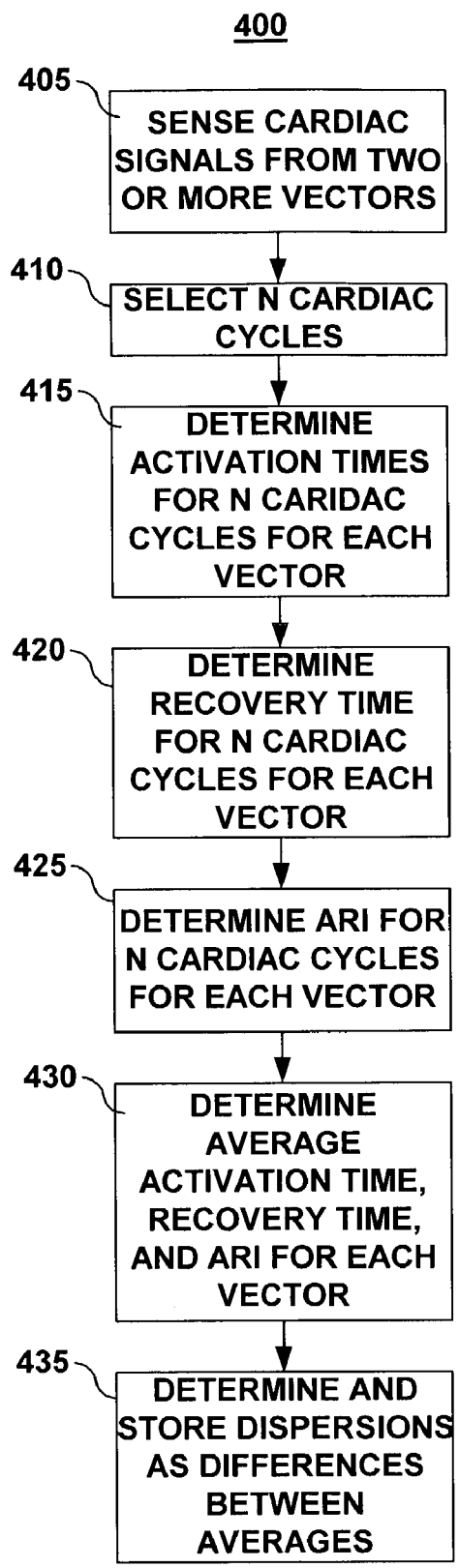
FIG. 7 is a flow chart summarizing the steps included in an alternative method for measuring dispersion of activation, recovery, and/or ARI.

FIG. 7 is a flow chart summarizing the steps included in an alternative method for measuring dispersion of activation, recovery, and/or ARI. At step 405, the cardiac signals from the selected sensing vectors are sensed. At step 410, a predetermined number of cardiac cycles are selected for measuring dispersion. Two or more cardiac cycles may be selected, preferably on the order of 3 to 10 cardiac cycles.

At step 415, the activation times for each vector during each of the selected cardiac cycles are determined. At step 420, the recovery times for each vector during each of the selected cardiac cycles are determined. Determination of activation time and recovery time for each vector is performed as described above. At step 425, the ARIs for each vector during each cardiac cycle are determined as the differences of the respective activation times and recovery times.

At step 430, the measured activation times, recovery times and ARIs for each sensing vector are averaged over the selected number of cardiac cycles. At step 435, the dispersions of activation, recovery and/or ARI are determined based on the differences between the activation times, recovery times, and ARIs, respectively, averaged over the selected number of cardiac cycles.

Figure 8:
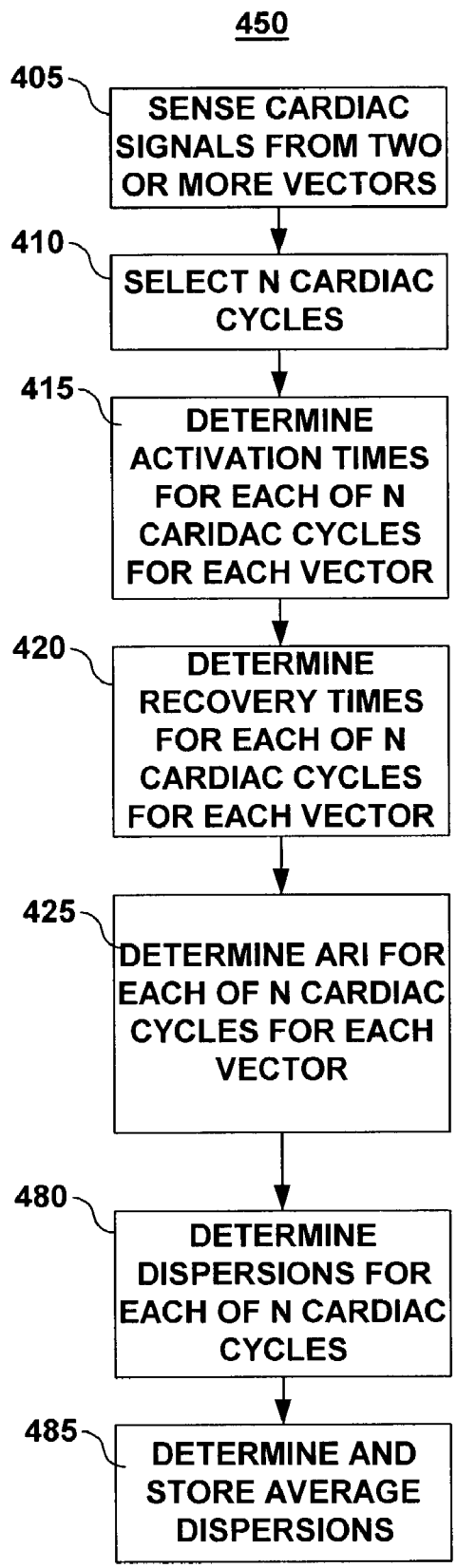
FIG. 8 is a flow chart summarizing the steps included in yet another alternative method for measuring dispersion of activation, recovery and/or ARI.

FIG. 8 is a flow chart summarizing the steps included in yet another alternative method for measuring dispersion of activation, recovery and/or ARI. Identically-numbered steps 405 through 420 correspond to steps 405 through 420 of method 400 of FIG. 7. After determining the activation times, recovery times, and ARI for each sensing vector during each of the selected cardiac cycles, the dispersions for activation time, recovery time, and/or ARI during each cardiac cycle are determined at step 455 as the measured parameter differences between the selected sensing vectors during each of the selected cardiac cycles. At step 460, the dispersions determined for each parameter for each of the selected cardiac cycles are averaged over the selected number of cardiac cycles to determine an overall average dispersion for a given parameter. This average dispersion is stored at step 460.

Thus the dispersions of activation, recovery, and/or ARIs measured according to the present invention are the difference in activation times, recovery times, and ARIs, respectively, measured during the same cardiac cycle using different local and/or global sensing vectors. An average dispersion may be calculated by averaging the dispersions measured over a selected number of cardiac cycles (method 450 of FIG. 8) or by calculating the differences between averaged activation times, recovery times and/or ARI measured over a selected number of cardiac cycles (method 400 of FIG. 7).

Figure 9:
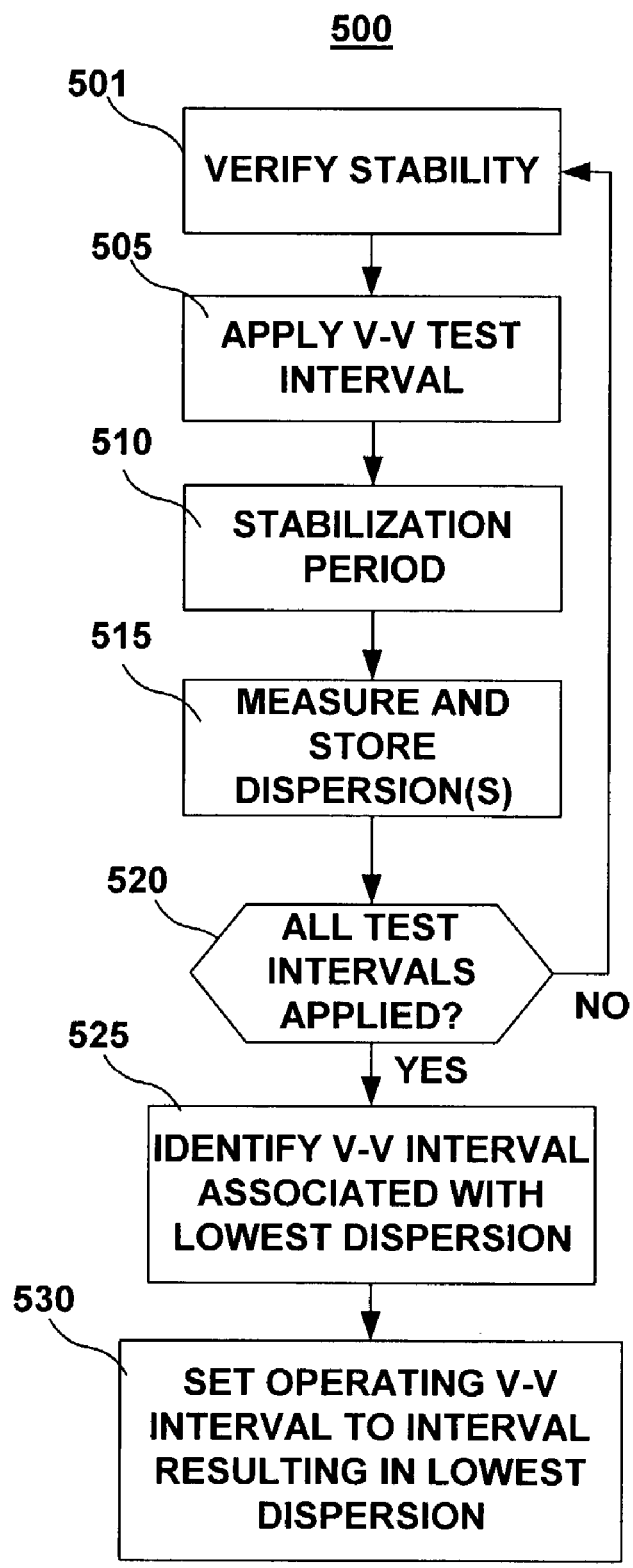
FIG. 9 is a flow chart summarizing the steps included in one method for automatically adjusting inter-ventricular (V-V) intervals during cardiac resynchronization therapy based on measures of electrical dispersion.

As noted previously in conjunction with FIG. 3, determination of an increase in dispersion may be used to trigger or adjust the delivery of a therapy. FIG. 9 is a flow chart summarizing the steps included in one method for automatically adjusting inter-ventricular (V-V) intervals during cardiac resynchronization therapy based on measures of electrical dispersion. Method 500 is an iterative procedure for testing the effects of varying V-V intervals on electrical dispersion. Preferably, method 500 is performed under stable physiological conditions, as verified at step 501, to eliminate anomalous results to due fluctuating heart rate, respiration rate, activity level, premature heart beats or other cardiac depolarization rate changes, etc. Stability verification may include, but is not limited to, heart rate stability, respiration rate stability, and/or activity level stability. Heart rate stability may be verified based on algorithms known in the art. For example heart rate stability may be verified based on cycle length variability criteria. Respiration rate and activity level stability may be verified based on respiration sensor signals and activity sensor signals, respectively, which are known for use with implantable medical devices.

After verifying physiologic stability, first V-V test interval applied at step 505. A set of test V-V intervals may be predetermined and include simultaneous left and right ventricular pacing (a V-V interval of 0 ms), right ventricular pacing leading left ventricular pacing by one or more increments, and left ventricular pacing leading right ventricular pacing by one or more increments.

At step 510, a stabilization period is applied to allow the response to a new V-V interval to reach a steady state before measuring electrical dispersion. The stabilization period may be predefined and may range from a few cardiac cycles to several minutes.

At step 515, dispersion of the parameter(s) of interest is measured. Dispersion of activation, recovery, and or ARI may be measured during one selected cardiac cycle according to method 350 of FIG. 4. Alternatively, an average dispersion may be measured over a selected number of cardiac cycles according to method 400 of FIG. 7 or method 450 of FIG. 8. The measured dispersion(s) are stored at step 515 with the applied V-V test interval.

At step 520, method 500 determines if all V-V test intervals have been applied. If not, method 500 returns to step 501 to re-verify physiologic stability before applying the next V-V test interval and repeating steps 510 and 515 for measuring electrical dispersion during pacing at the new test interval. The entire testing procedure is preferably performed at approximately the same, stable heart rate, and/or other physiologic conditions. Once all test intervals have been applied, the V-V interval associated with the lowest measured dispersion is identified at step 525. At step 530, the operating V-V interval is automatically adjusted to the interval identified at step 525.

Method 500 can be performed by an IMD, such as IMD 10 shown in FIG. 2, upon receipt of a command by a clinician using an external programming device. Method 500 may be repeated on a periodic basis to ensure the V-V interval resulting in the lowest electrical dispersion is maintained. Alternatively or additionally, method 500 is performed in response to an increase in dispersion during dispersion monitoring according to method 325 of FIG. 3.

Thus, a system and method have been described for monitoring electrical dispersion using an implantable medical device capable of sensing local EGM and/or global EGM and/or subcutaneous ECG signals. A worsening of heart failure and/or and increased risk of arrhythmias is indicated by an increase in electrical dispersion. Accordingly, a therapy may be adjusted or triggered upon detected increases in electrical dispersion. While the present invention has been described according to specific embodiments presented herein, these embodiments are intended to be exemplary, not limiting, with regard to the following claims.

The invention claimed is:

1. A method for monitoring a heart, comprising:
detecting a plurality of localized electrogram (EGM) signals associated with electrical activity of a heart at a plurality of sensing sites, wherein a plurality of addressable electrodes produce a plurality of sensing vectors at the plurality of sensing sites within a single chamber of the heart;
measuring an activation time for a given cardiac cycle for each of the detected plurality of localized EGM signals;
measuring a recovery time for the given cardiac cycle from each of the detected plurality of localized EGM signals;
calculating an activation recovery interval as the difference between the activation time and the recovery time for each said detected plurality of localized EGM signals; and
calculating at least a one of: a dispersion of activation time, a recovery time, an activation recovery interval based on the detected plurality of localized EGM signals.

2. A method according to claim 1, wherein in the event that a comparison of the value of an earlier calculated activation recovery interval with a subsequently calculated activation recovery interval reveals a temporally increasing activation recovery interval, then:
declaring a worsening heart failure condition.

3. A method according to claim 1, wherein in the event that a comparison of the value of an earlier calculated activation recovery interval with a subsequently calculated activation recovery interval reveals a temporally increasing activation recovery interval, then:
declaring an increased risk for arrhythmias.

4. A method according to claim 1, further comprising:
delivering a cardiac pacing therapy in response to a relative increase in the activation recovery interval dispersion between a prior and a subsequent calculation of the activation recovery interval.

5. A method according to claim 1, further comprising:
adjusting a cardiac pacing therapy until a relative decrease occurs in the activation recovery interval between a prior and a subsequent calculation of the activation recovery interval.

6. An apparatus for monitoring a heart, comprising:
means for detecting a plurality of localized electrogram (EGM) signals associated with electrical activity of a heart at a plurality of sensing sites, wherein a plurality of addressable electrodes produce a plurality of sensing vectors at the plurality of sensing sites disposed within a single chamber of the heart;
means for measuring an activation time for a given cardiac cycle for each of the detected plurality of localized EGM signals;
means for measuring a recovery time for the given cardiac cycle from each of the detected plurality of localized EGM signals;
means for calculating an activation recovery interval as the difference between the activation time and the recovery time for each said detected plurality of localized EGM signals; and
means for calculating at least a one of: a dispersion of activation time, a recovery time, an activation recovery interval.

7. An apparatus according to claim 6, wherein in the event that a comparison of the value of an earlier calculated activation recovery interval with a subsequently calculated activation recovery interval reveals a temporally increasing activation recovery interval, then:

means for declaring a worsening heart failure condition.

8. An apparatus according to claim 6, wherein in the event that a comparison of the value of an earlier calculated activation recovery interval with a subsequently calculated activation recovery interval reveals a temporally increasing activation recovery interval, then further comprising:

means for declaring an increased risk for arrhythmias.

9. An apparatus according to claim 6, further comprising:

means for delivering a cardiac pacing therapy in response to a relative increase in the activation recovery interval dispersion between a prior and a subsequent calculation of the activation recovery interval.

10. An apparatus according to claim 6, further comprising:

means for adjusting a cardiac pacing therapy until a relative decrease occurs in the activation recovery interval between a prior and a subsequent calculation of the activation recovery interval.

11. An apparatus according to claim 6, further comprising:

an implantable medical device (IMD) housing the apparatus; and electronic circuitry means operatively disposed within the IMD for operatively carrying out the plurality of recited functions.

12. An apparatus according to claim 11, wherein the IMD comprises therapy delivery means for delivering a therapy responsive to the calculated one of: the dispersion of activation time, the recovery time, the activation recovery interval.

13. An apparatus according to claim 12, wherein the IMD comprises one of: a drug delivery device, a spinal cord stimulation device, a dual chamber pacemaker, a cardiac resynchronization device, a cardioverter-defibrillator.

14. An apparatus according to claim 12, further comprising:

means for setting a logical flag to a high-alert condition responsive to the calculated one of: the dispersion of activation time, the recovery time, the activation recovery interval.

15. An apparatus according to claim 14, wherein the logical flag comprises one of an increased-tachyarrhythmia risk condition and a worsening heart function condition.

16. A computer readable medium for storing instructions providing control signals via a computer processor, comprising:

instructions for detecting a plurality of localized electrogram (EGM) signals associated with electrical activity of a heart at a plurality of sensing sites, wherein a plurality of addressable electrodes produce a plurality of sensing vectors at the plurality of sensing sites disposed within a single chamber of the heart;

instructions for measuring an activation time for a given cardiac cycle for each of the detected plurality of localized EGM signals;

instructions for measuring a recovery time for the given cardiac cycle from each of the detected plurality of localized EGM signals;

instructions for calculating an activation recovery interval as the difference between the activation time and the recovery time for each said detected plurality of localized EGM signals; and instructions for calculating at least a one of: a dispersion of activation time, a recovery time, an activation recovery interval.

17. A computer readable medium according to claim 16, wherein in the event that a comparison of the value of an earlier calculated activation recovery interval with a subsequently calculated activation recovery interval reveals a temporally increasing activation recovery interval, then:

instructions for declaring a worsening heart failure condition.

18. A computer readable medium according to claim 16, wherein in the event that a comparison of the value of an earlier calculated activation recovery interval with a subsequently calculated activation recovery interval reveals a temporally increasing activation recovery interval, then further comprising:

instructions for declaring an increased risk for arrhythmias.

19. A computer readable medium according to claim 16, further comprising:

instructions for delivering a cardiac pacing therapy in response to a relative increase in the activation recovery interval dispersion between a prior and a subsequent calculation of the activation recovery interval.

20. A computer readable medium according to claim 16, further comprising:

instructions for adjusting a cardiac pacing therapy until a relative decrease occurs in the activation recovery interval between a prior and a subsequent calculation of the activation recovery interval.

21. A computer readable medium according to claim 16, further comprising:

an implantable medical device (IMD); and electronic circuitry means coupled to the computer readable medium for operatively carrying out the instructions.

22. A computer readable medium according to claim 21, wherein the IMD comprises therapy delivery means for delivering a therapy responsive to the calculated one of: the dispersion of activation time, the recovery time, the activation recovery interval.

23. A computer readable medium according to claim 22, wherein the IMD comprises one of: a drug delivery device, a spinal cord stimulation device, a dual chamber pacemaker, a cardiac resynchronization device, a cardioverter-defibrillator.

* * * * *